US010960013B2

(12) United States Patent
Van Dross

(10) Patent No.: US 10,960,013 B2
(45) Date of Patent: Mar. 30, 2021

(54) J-SERIES PROSTAGLANDIN-ETHANOLAMIDES AS NOVEL THERAPEUTICS FOR SKIN AND/OR ORAL DISORDERS

(71) Applicant: East Carolina University, Greenville, NC (US)

(72) Inventor: Rukiyah T. Van Dross, Winterville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 16/081,692

(22) PCT Filed: Mar. 2, 2017

(86) PCT No.: PCT/US2017/020315
§ 371 (c)(1),
(2) Date: Aug. 31, 2018

(87) PCT Pub. No.: WO2017/151836
PCT Pub. Date: Sep. 8, 2017

(65) Prior Publication Data
US 2019/0091238 A1     Mar. 28, 2019

Related U.S. Application Data

(60) Provisional application No. 62/303,679, filed on Mar. 4, 2016.

(51) Int. Cl.
| *A61K 31/5575* | (2006.01) |
| *A61K 45/06* | (2006.01) |
| *A61P 17/12* | (2006.01) |
| *A61P 35/00* | (2006.01) |
| *A61K 9/00* | (2006.01) |

(52) U.S. Cl.
CPC ........ *A61K 31/5575* (2013.01); *A61K 9/0014* (2013.01); *A61K 45/06* (2013.01); *A61P 17/12* (2018.01); *A61P 35/00* (2018.01)

(58) Field of Classification Search
CPC ............ A61K 31/5575; A61K 2300/00; A61K 45/06; A61K 9/0014; A61P 17/12; A61P 35/00
See application file for complete search history.

(56) References Cited

U.S. PATENT DOCUMENTS

| 3,710,795 A | 1/1973 | Higuchi et al. |
| 3,817,837 A | 6/1974 | Rubenstein et al. |
| 3,927,193 A | 12/1975 | Hansen et al. |
| RE28,819 E | 5/1976 | Thompson |
| 4,044,126 A | 8/1977 | Cook et al. |
| 4,328,245 A | 5/1982 | Yu et al. |
| 4,331,647 A | 5/1982 | Goldenberg |
| 4,348,376 A | 9/1982 | Goldenberg |
| 4,358,603 A | 11/1982 | Yu |
| 4,361,544 A | 11/1982 | Goldenberg |
| 4,364,923 A | 12/1982 | Cook et al. |
| 4,374,925 A | 2/1983 | Litman et al. |
| 4,409,239 A | 10/1983 | Yu |
| 4,410,545 A | 10/1983 | Yu et al. |
| 4,414,209 A | 11/1983 | Cook et al. |
| 4,444,744 A | 4/1984 | Goldenberg |
| 4,468,457 A | 8/1984 | Goldenberg et al. |
| 4,474,893 A | 10/1984 | Reading |
| 4,479,895 A | 10/1984 | Auditore-Hargreaves |
| 4,522,811 A | 6/1985 | Eppstein et al. |
| 4,624,846 A | 11/1986 | Goldenberg |
| 4,818,709 A | 4/1989 | Primus et al. |
| 4,946,778 A | 8/1990 | Ladner et al. |
| 5,033,252 A | 7/1991 | Carter |
| 5,052,558 A | 10/1991 | Carter |
| 5,323,907 A | 6/1994 | Kalvelage |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,914,322 A | 6/1999 | Falk et al. |
| 5,948,433 A | 9/1999 | Burton et al. |
| 5,952,366 A | 9/1999 | Pandey et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |

(Continued)

FOREIGN PATENT DOCUMENTS

| EP | 0172963 | 3/1986 |
| EP | 1307538 | 1/2009 |

(Continued)

OTHER PUBLICATIONS

Abdelrahman et al., Cardiovascular Research 65 (2005), 772-781, (Year: 2005).*
Soliman et al., Molecular Carcinogenesis 55:117-130, published online Jan. 3, 2015 (Year: 2015).*
Hill et al. Melanoma Management, vol. 1, No. 2, Dec. 4, 2014. (Year: 2014).*
https://www.chemicool.com/definition/derivative.html, (Year: 2020).*
International Search Report and the Written Opinion of the International Searching Authority corresponding to International Patent Application No. PCT/US2017/020315 (8 pages) (dated Jun. 29, 2017).
Adinolfi et al. "Anticancer activity of anandamide in human cutaneous melanoma cells" European Journal of Pharmacology, 718(1-3):154-159 (2013) (Abstract only).

(Continued)

*Primary Examiner* — Jean P Cornet
(74) *Attorney, Agent, or Firm* — Myers Bigel, P.A.

(57) ABSTRACT

Provided is a method of preventing and/or treating a skin disorder and/or an oral disorder including administering to a subject in need thereof an effective amount of a compound of formula (I) or a prodrug or derivative thereof, and salts thereof.

9 Claims, 5 Drawing Sheets

(56) References Cited

U.S. PATENT DOCUMENTS

| | | | |
|---|---|---|---|
| 6,010,715 A | 1/2000 | Wick et al. | |
| 6,024,975 A | 2/2000 | D'Angelo et al. | |
| 6,039,975 A | 3/2000 | Shah et al. | |
| 6,048,736 A | 4/2000 | Kosak | |
| 6,060,082 A | 5/2000 | Chen et al. | |
| 6,071,495 A | 6/2000 | Unger et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,680,299 B2 | 1/2004 | Or et al. | |
| 7,635,708 B2 * | 12/2009 | Spiegelman | A61K 31/425 514/369 |
| 8,637,679 B2 | 1/2014 | Mandal et al. | |
| 8,785,423 B2 | 7/2014 | Njar et al. | |
| 9,168,281 B2 | 10/2015 | Worden | |
| 9,328,060 B2 | 5/2016 | Van Dross et al. | |
| 2015/0111969 A1 | 4/2015 | Van Dross et al. | |

FOREIGN PATENT DOCUMENTS

| | | |
|---|---|---|
| WO | 2008118991 | 10/2008 |
| WO | 2014107655 | 7/2014 |
| WO | 2014182744 | 11/2014 |
| WO | 2019046556 | 3/2019 |

OTHER PUBLICATIONS

Arima et al. "The sarin-like organophosphorus agent bis(isopropyl methyl)phosphonate induces ER stress in human astrocytoma cells" The Journal of Toxicological Sciences, 41(5):617-625 (2016).
Bacelieri et al. "Cutaneous Warts: An Evidence-Based Approach to Therapy" American Family Physician, 72(4):647-652 (2005).
Boelens et al. "The Endoplasmic Reticulum: A Target for New Anticancer Drugs" In Vivo, 21:215-226 (2007).
Boyce et al. "A Selective Inhibitor of eIF2alpha Dephosphorylation Protects Cells from ER Stress" Science, 307(5711):935-939 (2005).
Christensen, Neil D. "Cottontail rabbit papillomavirus (CRPV) model system to test antiviral and immunotherapeutic strategies" Antiviral Chemistry & Chemotherapy, 16:355-362 (2005).
Chu et al. "Expression of CHOP in Squamous Tumor of the Uterine Cervix" The Korean Journal of Pathology, 46(5):463-469 (2012).
Cladel et al. "Wounding Prior to Challenge Substantially Improves Infectivity of Cottontail Rabbit Papillomavirus and Allows for Standardization of Infection" Journal of Virological Methods, 148(1-2):34-39 (2008).
Department of Health and Human Services, Food and Drug Administration "Guidance for Industry on Skin Irritation and Sensitization Testing of Generic Transdermal Drug Products; Availability" Federal Register/Notices, 65(23):5353-5354 Docket No. 99D-0236 (Feb. 3, 2000).
Farooqi et al. "Anticancer drugs for the modulation of endoplasmic reticulum stress and oxidative stress" Tumor Biology, 36(8):5743-5752 (2015).
Gaffal et al. "Cannabinoid 1 receptors in keratinocytes attenuate fluorescein isothiocyanate-induced mouse atopic-like dermatitis" Experimental Dermatology, 23(6):401-406 (2014) (Abstract only).
Glodde et al. "Differential role of cannabinoids in the pathogenesis of skin cancer" Life Sciences, 138:35-40 (2015).
Grimaldi et al. "The endocannabinoid system in the cancer therapy: an overview" Current Medicinal Chemistry, 18(11):1575-1583 (2011) (Abstract only).

Hassan et al. "Influenza A Viral Replication Is Blocked by Inhibition of the Inositol-requiring Enzyme 1 (IRE1) Stress Pathway" The Journal of Biological Chemistry, 287(7):4679-4689 (2012).
He, B. "Viruses, endoplasmic reticulum stress, and interferon responses" Cell Death and Differentiation, 13:393-403 (2006).
Kiraly et al. "Apigenin inhibits COX-2, PGE2, and EP1 and also initiates terminal differentiation in the epidermis of tumor bearing mice" Prostaglandins, Leukotrienes, and Essential Fatty Acids, 104:44-53 (2016) (Abstract only).
Kuc et al. "Arachidonoyl ethanolamide (AEA)-induced Apoptosis is Mediated by J-series Prostaglandins and is Enhanced by Fatty Acid Amide Hydrolase (FAAH) Blockade" Molecular Carcinogenesis, 51(2):139-149 (2012).
Ladin et al. "Synthesis and Evaluation of the Novel Prostamide, 15-Deoxy,delta 12,14-Prostamide J2, as a Selective Antitumor Therapeutic" Molecular Cancer Therapeutics, 16(5):838-849 (2017).
Leung et al. "Activation of the Unfolded Protein Response by 2-Deoxy-D-Glucose Inhibits Kaposi's Sarcoma-Associated Herpesvirus Replication and Gene Expression" Antimicrobial Agents and Chemotherapy, 56(11):5794-5803 (2012).
Li et al. "The expanding roles of endoplasmic reticulum stress in virus replication and pathogenesis" Critical Reviews in Microbiology, 41(2):150-164 (2015).
McLaughlin et al. "Cutaneous Warts" The Journal of Hand Surgery, 36(2):343-344 (2011) (Abstract only).
Milstein et al. "Hybrid hybridomas and the production of bi-specific monoclonal antibodies" Immunology Today, 5(10):299-304 (1984) (Abstract only).
Mulvey et al. "Maintenance of Endoplasmic Reticulum (ER) Homeostasis in Herpes Simplex Virus Type 1-Infected Cells through the Association of a Viral Glycoprotein with PERK, a Cellular ER Stress Sensor" Journal of Virology, 81 (7):3377-3390 (2007).
Nicolaou et al. "Synthesis and Biological Investigation of delta(12)-Prostaglandin J3 (delta(12)-PGJ3) Analogues and Related Compounds" Journal of the American Chemical Society, 138(20):6550-6560 (2016) (Abstract only).
Perry et al. "Antiviral Activity of a Small Molecule Deubiquitinase Inhibitor Occurs via Induction of the Unfolded Protein Response" PLoS Pathogens, 8(7):e1002783 (2012).
Polin et al. "Monoclonal Antibodies Against Microorganisms" European Journal of Clinical Microbiology, 3(5):387-398 (1984).
Rakestraw et al. "Antibody-targeted photolysis: In vitro studies with Sn(IV) chlorin e6 covalently bound to monoclonal antibodies using a modified dextran carrier" Proceedings of the National Academy of Sciences USA, 87:4217-4221 (1990).
Rider et al. "Broad-Spectrum Antiviral Therapeutics" PLoS One, 6(7):e22572 (2011).
Sanfilippo et al. "Common pediatric and adolescent skin conditions" Journal of Pediatric and Adolescent Gynecology, 16(5):269-283 (2003) (Abstract only).
Soderstrom et al. "Cannabinoids Modulate Neuronal Activity and Cancer by CB1 and CB2 Receptor-Independent Mechanisms" Frontiers in Pharmacology, 8(720):1-28 (2017).
Soliman et al. "Anandamide-induced endoplasmic reticulum stress and apoptosis are mediated by oxidative stress in non-melanoma skin cancer: Receptor-independent endocannabinoid signaling" Molecular Carcinogenesis, 55(11):1807-1821 (2016) (Abstract only).
Soliman et al. "Arachidonoyl-ethanolamide activates endoplasmic reticulum stress-apoptosis in tumorigenic keratinocytes: Role of cyclooxygenase-2 and novel J-series prostamides" Molecular Carcinogenesis, 55(2):117-130 (2016) (Abstract only).
Toth et al. "Endoplasmic Reticulum Stress as a Novel Therapeutic Target in Heart Diseases" Cardiovascular & Hematological Disorders-Drug Targets, 7(3):205-218 (2007) (Abstract only).
Van Dross, Rukiyah T. "Metabolism of anandamide by COX-2 is necessary for endocannabinoid-induced cell death in tumorigenic keratinocytes" Molecular Carcinogenesis, 48(8):724-732 (2009) (Abstract only).
Van Dross et al. "Constitutively Active K-cyclin/cdk6 Kinase in Kaposi Sarcoma-Associated Herpesvirus-Infected Cells" Journal of the National Cancer Institute, 97(9):656-666 (2005).
Van Dross et al. "Do Truncated Cyclins Contribute to Aberrant Cyclin Expression in Cancer?" Cell Cycle, 5(5):472-477 (2006).

(56) References Cited

OTHER PUBLICATIONS

Van Dross et al. "Receptor-dependent and Receptor-independent Endocannabinoid Signaling: A Therapeutic Target for Regulation of Cancer Growth" Life Sciences, 92(8-9):463-466 (2013).

Elhassanny et al. "Prostaglandin D2-ethanolamide induces skin cancer apoptosis by suppressing the activity of antioxidants" Prostaglandins and Other Lipid Mediators, 142:9-23 (2019) cellular.

Matias et al. "Prostaglandin Ethanolamides (Prostamides): In Vitro Pharmacology and Metabolism" The Journal of Pharmacology and Experimental Therapeutics, 309(2):745-757 (2004).

Kaplan et al. "Peroxisome Proliferatory-activated Receptor γ is Required for the Inhibitory Effect of Ciglitazone but not 15-Deoxy-Δ12,14-Prostaglandin J2 on the NfKb Pathway in Human Endothelial Cells" SHOCK, vol. 28, No. 6, pp. 722Y726 (2007).

Koyani et al. "15-deoxy-Δ12,14-PGJ2 promotes inflammation and apoptosis in cardiomyocytes via the DP2/MAPK/TNFα axis" International Journal of Cardiology 173: 472-480 (2014).

Powell, William S. "15-deoxy-Δ12,14-PGJ2: endogenous PPARγ ligand or minor eicosanoid degradation product?" Clin Invest. 112(6):828-830 (2003).

Ray et al. "The Peroxisome Proliferator-Activated Receptor γ (PPARγ) Ligands 15-Deoxy-Δ12,14-Prostaglandin J2 and Ciglitazone Induce Human B Lymphocyte and B Cell Lymphoma Apoptosis by PPARγ-Independent Mechanisms" J Immunol, 177:5068-5076 (2006).

Surh et al. "15-deoxy-Δ12,14-prostaglandin J2, an electrophilic lipid mediator of anti-inflammatory and pro-resolving signaling" Biochemical Pharmacology 82: 1335-1351 (2011).

Wang et al. "Induction of apoptosis by 15d-PGJ2 via ROS formation: An alternative pathway without PPARγ activation in non-small cell lung carcinoma A549 cells" Prostaglandins & other Lipid Mediators 94:104-111 (2011).

\* cited by examiner

J-SERIES PROSTAGLANDIN-ETHANOLAMIDES AS NOVEL THERAPEUTICS FOR SKIN AND/OR ORAL DISORDERS

RELATED APPLICATION INFORMATION

This application claims the benefit of and priority to U.S. Provisional Patent Application Ser. No. 62/303,679, filed Mar. 4, 2016, the disclosure of which is incorporated herein by reference in their entirety.

FIELD OF THE INVENTION

The present invention relates to methods of using and administering J-series prostaglandin-ethanolamides and prodrugs thereof for treatment and/or prevention of skin and/or oral disorders.

BACKGROUND OF THE INVENTION

15deoxy, Δ12,14 Prostaglandin J2 (15dPGJ2-EA; see U.S. Pat. No. 9,328,060) is a novel molecule that was discovered and synthesized by our research group. We determined that 15dPGJ2-EA induced skin tumor cell death while causing little harm to non-tumor skin cells.

The endoplasmic reticulum (ER) is an organelle that is primarily responsible for folding proteins. ER stress occurs when the demand for protein folding exceeds the cells capacity to fold proteins leading to an accumulation in unfolded or misfolded proteins. In response to the accumulation of malformed proteins the cell attempts to relieve the stress or initiates death if the total cellular stress is insurmountable.

SUMMARY OF THE INVENTION

In an aspect of the invention, provided is a compound, 15-deoxy $\Delta^{12,14}$-prostagladin $J_2$-ethanolamide (15-deoxy $\Delta^{12,14}PGJ_2$-EA), of formula (I), or a prodrug or derivative thereof, and salts thereof:

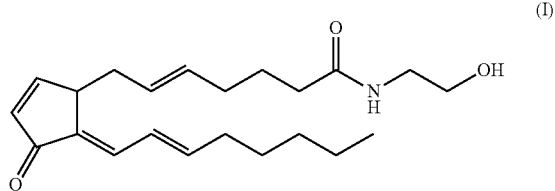 [SMILES: CCCCC/C=C/C=C1/C(=O)C=CC1C/C=C/CCCC(=O)NCCO]

(I)

as well as pharmaceutical compositions comprising a therapeutically effective amount of 15-deoxy $\Delta^{12,14}PGJ_2$-EA, or a prodrug or derivative thereof, and salts thereof, and a pharmaceutically acceptable carrier. Also provided are methods of preventing and/or treating a skin disorder and/or oral disorder in a subject, the method comprising administering a compound and/or composition described herein.

Embodiments of the present invention also provide kits comprising the compounds and/or compositions described herein and a container suitable for housing or delivery of the compounds and/or composition within a common packaging, and instructions for use of the same for the prevention or treatment of skin and/or oral disorders.

DETAILED DESCRIPTION

Figure 1:
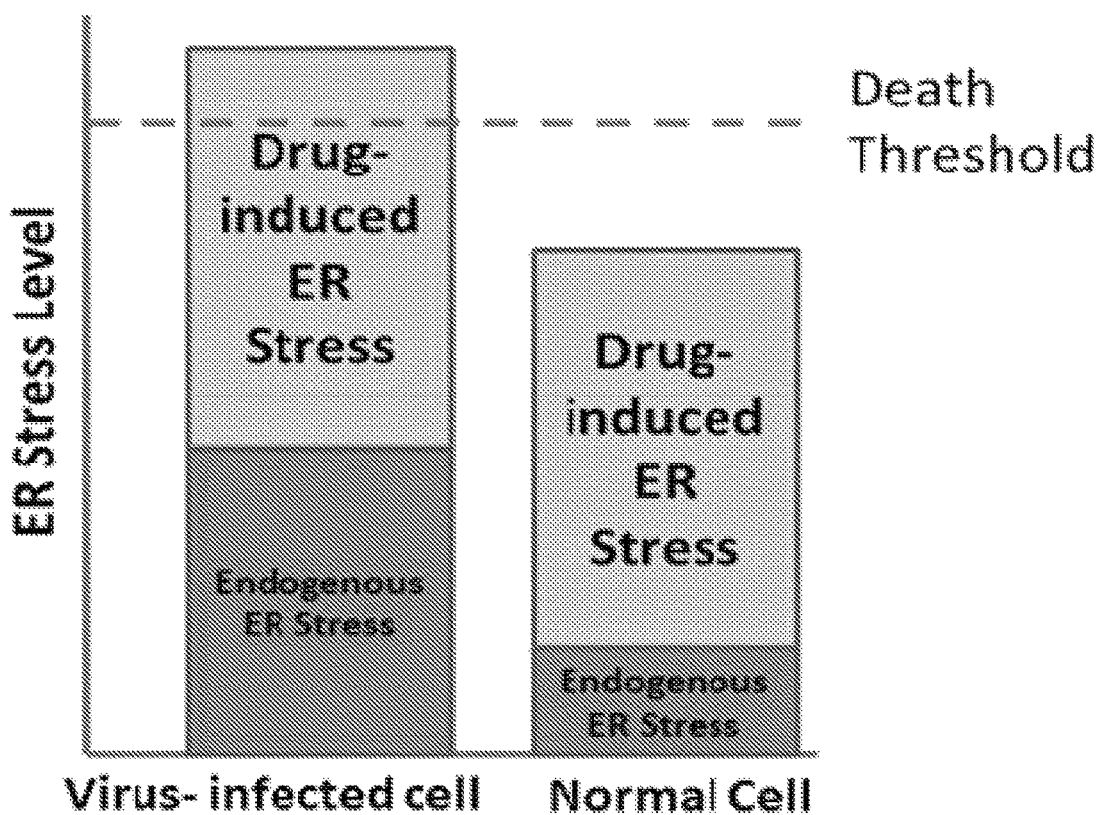
FIG. 1 is a graph illustrating that ER stress is elevated in virus-infected cells, but not in normal cells. Exposure to ER stress inducing agents causes the total cellular level of ER stress to exceed the death threshold in virus-infected cells, thereby causing selective toxicity.

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

The invention includes numerous alternatives, modifications, and equivalents as will become apparent from consideration of the following detailed description.

As used herein, the singular forms "a," "an" and "the" are intended to include the plural forms as well, unless the context clearly indicates otherwise. For example, "a" cell can mean one cell or a plurality of cells.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims or figures unless specifically indicated otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount. For example, "about X" where X is a measurable value, is meant to include X as well as variations of +20%, ±10%, ±5%, ±1%, ±0.5%, or even ±0.1% of X. A range provided herein for a measureable value may include any other range and/or individual value therein.

As used herein, the transitional phrase "consisting essentially of" means that the scope of a claim is to be interpreted to encompass the specified materials or steps recited in the claim, and those that do not materially affect the basic and novel characteristic(s) of the claimed invention.

As used herein, "one or more" can mean one, two, three, four, five, six, seven, eight, nine, ten or more, up to any number.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

The term "administering" or "administered" as used herein is meant to include topical, parenteral and/or oral administration, all of which are described herein. Parenteral administration includes, without limitation, intravenous, intraperitoneal, subcutaneous and/or intramuscular administration (e.g., skeletal muscle or cardiac muscle administration). In the methods of this invention, a compound or composition of this invention may be administered alone and/or simultaneously with one or more other compounds. In some embodiments, the compounds may be administered sequentially, in any order. It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, topical, rectal, intraperitoneal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

"15-deoxy $\Delta^{12,14}$PGJ$_2$-EA," "15dD12,14-PGJ-EA" or "15d-PGJ-EA" refer to 15-deoxy $\Delta^{12,14}$-prostagladin J$_2$-ethanolamide as set forth in formula (I):

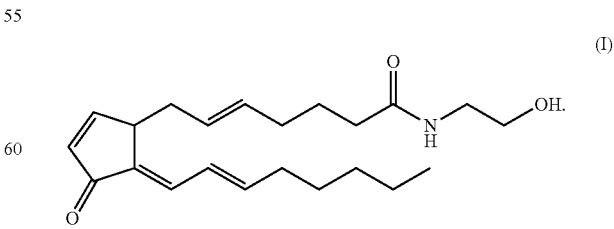

(I)

"Prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound.

Particular prodrugs of the present invention include Prostaglandin $D_2$ ethanolamide (PGD$_2$-EA") as set forth in formula (II):

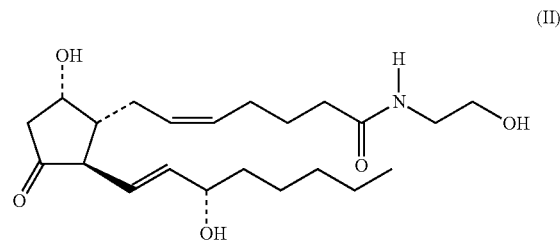 [SMILES: CCCCC[C@H](O)/C=C/[C@H]1C(=O)C[C@H](O)[C@@H]1C/C=C\CCCC(=O)NCCO]

(II)

"Salt" or "pharmaceutically acceptable salt" as used herein refers to a salt that retains the biological effectiveness of the free acids and bases of a specified compound and is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates. In particular embodiments, the salt is a hydrochloride, sulfite, benzoate, salicykate, cocoate, tallowate, undecylenate or carboxylate salt.

Provided herein are compounds, compositions, and methods for treating and/or preventing skin and/or oral disorders. In some embodiments, the skin and/or oral disorder is a noncancerous or precancerous disorder. In some embodiments, a method of the present invention is selectively toxic to cells having an increased level of ER stress compared to normal cells of the same type.

Studies with 15d-PGJ2-EA and tumor cells determined that the selective death in tumor cells was mediated by the induction of endoplasmic reticulum (ER) stress. In some embodiments, a compound and/or composition of the present invention can induce ER stress in cells and can push cells with moderate or greater levels of ER stress beyond their death threshold. In contrast, normal cells may contain low endogenous ER stress, and an equivalent amount of the compound and/or composition will not result in cell death of the normal cells, thereby producing selective toxicity. Selectively targeting the diseased cells may decrease the risk of developing adverse effects.

In some embodiments, a method of the present invention may treat and/or prevent a skin and/or oral disorder that is associated with and/or mediated by increased ER stress. In some embodiments, a method of the present invention may treat and/or prevent a skin and/or oral disorder in which the skin and/or oral cells are exhibiting increased ER stress. In some embodiments, the increased ER stress is during the growth cycle of cells (e.g., infected cells). Cells treated by a method of the present invention may exhibit a level of ER stress that is at least about 10% (e.g., about 20%, 30%, 40%, 50%, 60%, 70%, 80%, 90%, 100%, 125%, 150%, 200%, or more) greater than the level of ER stress in a normal, healthy cell of the same type. The level of ER stress may be determined by the level of ER stress protein expression in the cells.

The endoplasmic reticulum (ER) stress pathway has emerged as a novel therapeutic target to selectively eliminate virus-containing cells. Numerous viruses such as the hepatitis virus, the human immunodeficiency virus (HIV), herpesvirus and human papillomavirus (HPV) rely on the ER stress pathway to process viral proteins, replicate, and survive. Cells infected with HPV can have elevated levels of ER stress. HPV is a worldwide cause of morbidity and mortality with clinical manifestations that include cervical cancer, anogenital cancer, genital warts and cutaneous warts.

Cutaneous warts are common benign growths that occur in approximately 10% of children and adolescents. Warts are contagious, recurrent, socially stigmatizing and can be resistant to therapy. These lesions typically are removed using liquid nitrogen cryotherapy, $CO_2$ laser vaporization, or topical chemotherapeutic approaches such as salicylic acid and imiquimod. However, these therapeutic approaches can cause pain, permanent scarring, skin necrosis, nerve injury and local inflammation due to the impact of the procedure/agent on the uninvolved skin. As such, therapeutic strategies are desired that target virus-infected cells while causing minimal damage to uninfected cells. Our group discovered and synthesized the novel agent, 15deoxy, $\Delta^{12,14}$prostaglandin-ethanolamide (also known as 15deoxy, $\Delta^{12,14}$prostamide $J_2$ or 15dPMJ$_2$) which exhibited targeted toxicity in skin tumor cells and minimal toxicity in non-tumor skin cells due to the induction of ER stress.

Additionally, the ER is an intracellular organelle that is primarily responsible for folding newly synthesized proteins. ER stress occurs when the protein-folding demand exceeds the protein-folding capacity thereby causing misfolded or unfolded proteins to accumulate. In response to ER stress, cells decrease global translation, increase synthesis of protein-folding enzymes, and degrade misfolded or unfolded proteins to resolve the ER stress and survive. However, when ER stress is too severe, the ER stress machinery becomes overloaded and apoptotic death is initiated. Viral proteins are synthesized in large quantities to facilitate replication, viral particle formation, and survival. This increased protein processing demand activates the ER stress pathway. One strategy for novel therapeutic development is to employ ER stress inducers to further elevate the level of ER stress, which ultimately can initiate cell death in virus infected cells. ER stress can selectively eliminate virus-infected cells because normal cells contain low endogenous ER stress levels that require higher levels of the ER stress inducer to initiate death compared to virus infected cells (FIG. 1). Since ER stress is elevated in HPV-infected but not uninfected cells 15dPMJ$_2$ may cause the ER stress machinery to be selectively overwhelmed in HPV-containing cells thereby facilitating its elimination.

Figure 2:
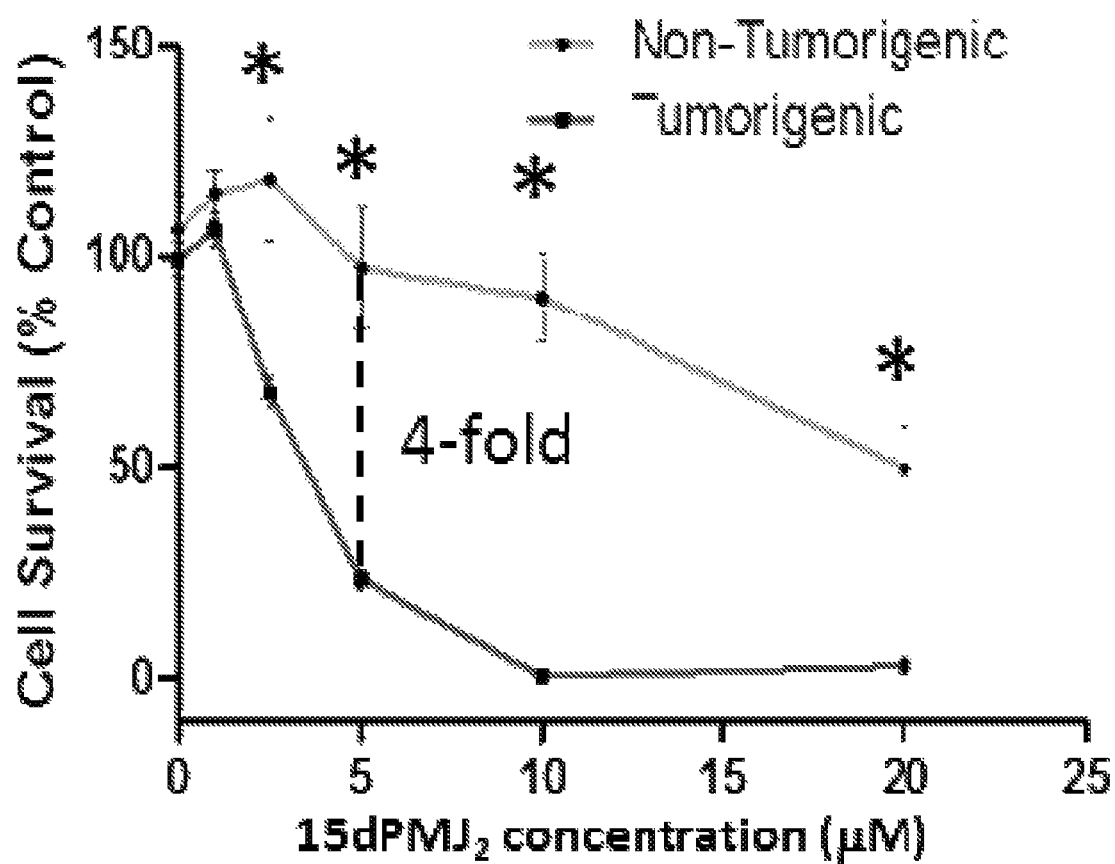
FIG. 2 is a graph illustrating that 15dPMJ2 is selectively toxic. Tumorigenic and non-tumorigenic keratinocytes were treated with different concentrations of 15dPMJ2, vehicle, or were untreated for 12 hours. Cell viability was detected by conducting MTS experiments. Data represent the mean±SEM of three independent experiments and are expressed as the percent of the untreated cells. *P<0.01.

We have demonstrated that arachidonoyl-ethanolamide (AEA) was metabolized to the novel Prostaglandin-ethanolamides (prostamide), 15dPMJ$_2$ by cyclooxygenase-2 (COX-2) (14-16). 15dPMJ$_2$ activates the ER stress pathway and is selectively toxic to tumor cells (FIG. 2).

Thus, methods of administration and use of the compounds and compositions described herein are directed to the treatment and/or prevention of skin and/or oral disorders. Accordingly, another embodiment of the present invention provides a method for administering to a subject in need thereof a compound or pharmaceutical composition as described herein for the prevention or treatment of skin disorders (including precancerous or noncancerous skin disorders) or oral disorders. In some embodiments, the skin and/or oral disorder may be a viral infection and/or caused by a viral infection. In some embodiments, a method of the present invention may treat and/or prevent a viral infection in a subject without cytotoxicity to cells that do not contain the virus (i.e., non-viral cells) or with reduced cytotoxicity to non-viral cells. In some embodiments, a method of the present invention may treat and/or prevent a skin and/or oral disorder in a subject without cytotoxicity to cells that do not have an increased level of ER stress or with reduced cytotoxicity to cells that do not have an increased level of ER stress. A method of the present invention may treat and/or prevent a skin and/or oral disorder in a subject with reduced non-viral cell cytotoxicity and/or reduced normal, healthy cell cytotoxicity compared to a different method for treating and/or preventing the skin and/or oral disorder, such as, for example, one that does not administer a compound and/or composition of the present invention.

In some embodiments, a method of the present invention may be cytotoxic to viral cells and/or cells having an increased level of ER stress compared to normal, healthy cells. The method may provide increased cytotoxicity to such cells compared to a different method for treating and/or preventing the skin and/or oral disorder, such as, for example, one that does not administer a compound and/or composition of the present invention. In some embodiments, the cytotoxicity may be increased by at least about 10%, 15%, 20%, 25%, 30%, 35%, 40%, 45%, 50%, 55%, 60%, 65%, 70%, 75%, 80%, 85%, 90%, 95%, 98%, 99%, 100%, 150%, or more compared to a different method for treating and/or preventing the skin and/or oral disorder. Cytotoxicity may be determined using methods known to those of skill in the art, such as, for example, a qualitative reading of hematoxylin & eosin (H&E) slides, a lactate dehydrogenase (LDH) assay and/or a 3-(4, 5-Dimethyl-2-thiazolyl)-2, 5-diphenyl-2H-tetrazolium bromide (MTT) assay.

For administration, either the compound or pharmaceutical composition is understood as being or comprising the active ingredient and capable of administration to a subject, and thus, in some instances, the terms are interchangeable. Non-limiting methods of administration include, but are not limited to oral, parenteral (e.g., subcutaneous, intramuscular, intradermal, intraperitoneal, or intravenous), inhalation spray (nasal and oral), topical (i.e., both skin and mucosal surfaces, including airway surfaces), transdermal, rectal, nasal, sublingual, buccal, or implanted reservoir administration, etc. In one embodiment, a composition of the present invention is administered topically or transdermally. In some embodiments, a composition of the present invention is administered topically. In yet another embodiment, a composition of the present invention is administered intraperitoneally.

The pharmaceutical compositions of the present invention may be suitably formulated for administration by any means known in the art. Non-limiting examples of forms of administration include, but are not limited to oral, parenteral (e.g., subcutaneous, intravenous, intramuscular, intra-articular, intra-synovial, intrasternal, intrathecal, intrahepatic, intralesional and intracranial injection or infusion techniques), inhalation spray (nasal and oral), topical (i.e., both skin and mucosal surfaces, including airway surfaces), transdermal, rectal, nasal, sublingual, buccal, or implanted reservoir administration, etc. In one embodiment, a composition of the present invention is administered topically or transdermally. For topical administration, suitable forms include, but are not limited to, suitable transdermal delivery systems known in the art, such as patches, and for nasal delivery, suitable forms include, but are not limited to, aerosol and nebulized delivery systems known in the art.

In some embodiments, a pharmaceutical composition of the present invention may be in the form suitable for topical administration. Non-limiting examples include, but are not limited to, pharmaceutical compositions in the form of a topical solution, ointment, cream, emulsion, a gel, a dispersion, a suspension, a foam, an aerosol, a droplet, an injectable form and/or a coating in which the active component may be suspended or dissolved in one or more carriers. A topical composition may be applied to body surfaces of a subject, including skin, mucous membranes, scalp, hair and/or nails. Carriers for topical administration of the compounds of this invention include, but are not limited to, mineral oil, liquid petrolatum, white petrolatum, propylene glycol, polyoxyethylene, polyoxypropylene compound, emulsifying wax and water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and water.

Methods of formulating pharmaceutical compositions have been described in numerous publications such as Pharmaceutical Dosage Forms: Tablets. Second Edition. Revised and Expanded. Volumes 1-3, edited by Lieberman et al.; Pharmaceutical Dosage Forms: Parenteral Medications. Volumes 1-2, edited by Avis et al.; and Pharmaceutical Dosage Forms: Disperse Systems. Volumes 1-2, edited by Lieberman et al.; published by Marcel Dekker, Inc, the disclosure of each of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

According to embodiments of the present invention, precancerous conditions include, but are not limited to, actinic keratosis, hypertrophic actinic keratosis, bowenoid actinic keratosis and actinic cheilitis.

According to still other embodiments of the present invention, skin disorders include, but are not limited to, skin cancer (basal and squamous cell carcinoma), acne, psoriasis, warts, herepes, rosacea, seborrheic eczema, hives (allergic or idiopathic urticaria), cutaneous candidiasis (fungi-mediated), carbuncles, cellulitis, impetigo, erysipelas, eczema, cancer sores (virus-mediated), cold sores, ichthyosis vulgaris, dermatomyositis, acrodermatitis, sebaceous cyst, keloid, lichen planus, corns, calluses, tinea versicolor, shingles (virus-mediated), congenital erythropoietic porphyria, dermatitis, contact dermatitis, Darier's disease, dystrophic epidermolysis bullosa, epidermolysis bullosa simplex, Hailey-hailey disease, hidradenitis, suppurativa, hirsutism, hyperhidrosis, ichthyosis, keratosis pilaris, melanoma, pemphigus vulgaris, scabies (mite-mediated), Sweet's syndrome, vitiligo, pyoderma gangrenosum, and pityriasis lechenoides. "Psoriasis" as used herein can refer to a chronic, relapsing/remitting, immune-mediated skin disease characterized by red, scaly patches, papules, and plaques, which may itch. There are generally five main types of psoriasis: plaque, guttate, inverse, pustular, and erythrodermic. Skin disorders also include disorders associated with ER stress.

According to further embodiments of the present invention, oral disorders include, but are not limited to, cold sores (virus-mediated), canker sores (virus-mediated), thrush (fungi-mediated), leukoplakia, dry mouth, stomatitis, glossitis, oral lichen planus, oral cancer, salivary gland stones, salivary gland tumors, pulpitis, dental abscess, gingivitis, periodontitis, receding gums, gingival hyperplasia and dry socket. Oral disorders also include disorders associated with ER stress.

In some embodiments, a method of the present invention may prevent and/or reduce the appearance and/or size of a wart. Example warts include, but are not limited to, common warts (verruca vulgaris), flat warts (verruca plana), filiform warts (verruca acuminate), mosaic warts, periungal warts, and/or plantar warts. In some embodiments, the wart may be induced and/or caused by a papillomavirus, such as a human papillomavirus.

A method of the present invention may reduce the appearance and/or size of a wart by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a benign lesion prior to administering of a compound and/or composition of the present invention. The appearance of the wart may be evaluated visually, such as, but not limited to, by the subject and/or a physician. The size of the wart may be determined using methods known to those of skill in the art.

In some embodiments, the subject may see a reduction in the size and/or appearance of a wart within 1, 2, 3, 4, 5, 6, 7, 8, 9, 10, 11, 12, 13, or more day(s) and/or week(s). In some embodiments, the method may reduce the size and/or appearance of a wart in the skin of the subject with 12 weeks or less, in some embodiments, within 8 weeks or less, and in further embodiments, within 4 weeks or less.

A method of the present invention may reduce the number of warts by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of warts prior to administering of a compound and/or composition of the present invention. The number of warts may be evaluated visually, such as, but not limited to, by the subject and/or a physician. The number of warts may be determined using methods known to those of skill in the art.

A method of the present invention may decrease the rate of recurrence of a wart in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of wart in the absence of administering of a compound and/or composition of the present invention. The rate of recurrence may be determined using methods known to those of skill in the art. For example, after a treatment and/or removal of a wart, the number of warts may be visually determined after a given period of time to determine the rate of recurrence.

In some embodiments, a method of the present invention may prevent and/or reduce the appearance and/or size of a precancerous or noncancerous lesion, such as, for example, a papular lesion, psoriasis, and/or macular lesion. In some embodiments, the precancerous or noncancerous lesion may be caused by and/or induced by a viral infection. In some embodiments, the precancerous or noncancerous lesion is a skin lesion. In some embodiments, the precancerous or noncancerous lesion may be induced and/or caused by a papillomavirus, such as a human papillomavirus. In some embodiments, at least a portion of or all of the cells in the precancerous or noncancerous lesion have an increased level of ER stress.

A method of the present invention may reduce the appearance and/or size of a precancerous or noncancerous lesion by at least about 5%, 10%, 15%, 20%, 25%, 30%, 35%, 40%, 45%, 50%, 55%, 60%, 65%, 70%, 75%, 80%, 85%, 90%, 95%, 97% or more compared to the appearance and/or size of the precancerous or noncancerous lesion prior to administering of a compound and/or composition of the present invention. The appearance of the precancerous or noncancerous lesion may be evaluated visually, such as, but not limited to, by the subject and/or a physician. The size of the precancerous or noncancerous lesion may be determined using methods known to those of skill in the art.

A method of the present invention may reduce the number of precancerous or noncancerous lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of precancerous or noncancerous lesions prior to administering of a compound and/or composition of the present invention. The number of precancerous or noncancerous lesions may be evaluated visually, such as, but not limited to, by the subject and/or a physician. The number of precancerous or noncancerous lesions may be determined using methods known to those of skill in the art.

A method of the present invention may decrease the rate of recurrence of a precancerous or noncancerous lesion in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of precancerous or noncancerous lesion in the absence of administering of a compound and/or composition of the present invention. The rate of recurrence may be determined using methods known to those of skill in the art. For example, after a treatment and/or removal of a precancerous or noncancerous lesion, the number of precancerous or noncancerous lesions may be visually determined after a given period of time to determine the rate of recurrence.

In some embodiments, the subject may be administered a second therapeutic agent and/or therapy (such as, e.g., antineoplastic chemotherapy or radiotherapy) prior to, at the same time, or after receiving a compound and/or composition of the present invention. The antineoplastic chemotherapy can be one or more of: folate antagonists, including methotrexate and pemetrexed; purine antagonists, including cladribine, clofarabine, fludarabine, 6-mercaptopurine, nelarabine, pentostatin; pyrimidine antagonists, including capecitabine, cytarabine, 5-fluorouracil, gemcitabine, hydroxyurea; biologic response modifiers, including interferon-alfa; bleomycin; DNA alkylating agents, including nitrosureas, carmustine, lomustine; DNA cross-linking drugs and alkylating agents, including bendamustine, chlorambucil, cyclophosphamide, ifosfamide, mechlorethamine (nitrogen mustard), melphalan, dacarbazine, temozolomide, procarbazine; asparaginase; antibiotics, including mitomycin; platinum complexes, including carboplatin, cisplatin, oxaliplatin; proteosome inhibitors, including bortezomib; spindle poisons, such as the taxanes (including docetaxel, paclitaxel, nab-paclitaxel (Abraxane®)) and the vincas (including vinblastine, vincristine, vinorelbine); topoisomerase inhibitors, such as the anthracyclines (including daunorubicin, daunomycin, doxorubicin, epirubicin), the camptothecines, (including irinotecan, topotecan), the podophyllotoxins (including etoposide, teniposide and mitoxantrone); tyrosine kinase inhibitors, (including erlotinib (Tarceva), gefitinib, imatinib, lapatinib, pazopanib, sorafenib, sunitinib); and ifosfamide.

It should also be understood that a specific dosage and treatment regimen for any particular patient will depend upon a variety of factors, including but not limited to, the age, body weight, general health, gender, diet, time of administration, rate of excretion, drug combination, and the judgment of the treating physician and the severity of the particular disease being treated.

In some embodiments, a compound and/or composition of the present invention may be administered (e.g., topically administered) to a subject using any method known to those of skill in the art. In some embodiments, the compound and/or composition may be administered (e.g., topically applied) to the subject at least 1, 2, 3, or more times per day. In some embodiments, the compound and/or composition may be administered (e.g., topically applied) to the subject at least 1, 2, 3, 4, 5, 6, 7, 8, or more times per week and/or month. In some embodiments, the compound and/or composition may be administered to the subject once daily, twice daily, every other day, every third day, once per week, or twice per week. In some embodiments, the compound and/or composition may be administered at least once daily for an extended period of time (e.g., a week, month, 2 months, etc.) and/or until the skin and/or oral disorder has been treated and/or prevented. In some embodiments, the compound and/or composition may be applied on an as needed basis.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. The human subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, drug screening, and/or drug development purposes.

The compounds of the present invention may be formulated as the sole pharmaceutically active ingredient in a composition of the present invention or may be combined with other active ingredients.

A composition of the present invention may contain one or more compounds of the present invention. In some embodiments, the compounds may be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof may be (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions may be effective for delivery of an amount, upon administration, that treats, prevents, and/or ameliorates one or more of the symptoms of diseases or disorders associated with a skin disorder and/or oral disorder.

In one embodiment, the compositions are formulated for single dosage administration. To formulate a composition, the weight fraction of a compound of the present invention is dissolved, suspended, dispersed or otherwise mixed in a selected carrier at an effective concentration such that the treated condition is relieved, prevented, or one or more symptoms may be ameliorated.

The active compound may be included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition may depend on absorption, inactivation and excretion rates of the active compound, the physicochemical characteristics of the compound, the dosage schedule, and/or the amount administered as well as other factors known to those of skill in the art. For example, the amount that is delivered may be sufficient to ameliorate one or more of the symptoms of a skin disorder and/or oral disorder as described herein.

In one embodiment, a therapeutically effective dosage should produce a serum concentration of the active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms may be prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion, gel, or the like. The form of the resulting mixture depends upon a number of factors, including the intended mode of administration and the solubility of the compound in the selected carrier or vehicle. The effective concentration may be sufficient for ameliorating the symptoms of the disease, disorder or condition treated and may be empirically determined.

The pharmaceutical compositions may be provided for administration to humans and/or animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions may, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient by weight of the composition, in one embodiment 0.1-95% by weight of the composition, in another embodiment 75-85% by weight of the composition, and in another embodiment 0.5%-50% by weight of the composition.

In some embodiments, a composition of the present invention may be suitable for oral administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, in one embodiment, capsules or tablets. The tablets, pills, capsules, troches and the like may contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, may be provided in a composition that protects it from the acidic environment of the stomach. For example, the composition may be formulated in an enteric coating that maintains its integrity in the stomach and releases the active compound in the intestine. The composition may also be formulated in combination with an antacid or other such ingredient. When the dosage unit form is a capsule, it may contain, in addition to material of the above type, a liquid carrier such as a fatty oil. In addition, dosage unit forms may contain various other materials which modify the physical form of the dosage unit, for example, coatings of sugar and other enteric agents. The compounds may be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials may also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(loweralkyl) acetals of loweralkyl aldehydes such as acetaldehyde diethyl acetal.

Parenteral administration, in one embodiment characterized by injection, either subcutaneously, intramuscularly or intravenously is also contemplated herein. Injectables may be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit-dose parenteral preparations may be packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized powders, which can be reconstituted for administration as solutions, emulsions and other mixtures, may also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures may be prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract may be in the form of an aerosol or solution for a nebulizer, or as a microtine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients may be administered. These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, may be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis, Pneumococcus, Hemophilis influenzae B, Treponema pallidum, Lyme disease, spirochetes, Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, may be appropriate for use as target agents with the compounds provided herein.

It should be noted that mixtures of antibodies and immunoglobulin classes may be used, as may hybrid antibodies. Multispecific, including bispecific and hybrid, antibodies and antibody fragments may be used in the methods of the present invention for detecting and treating target tissue and may comprise at least two different substantially monospecific antibodies or antibody fragments, wherein at least two of the antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. In some embodiments, fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair may be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorine6 via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein may also be conjugated to a ligand, such as an antibody, by using a coupling agent. Any bond which is capable of linking the components such that they are stable under physiological conditions for the time needed for administration and treatment is suitable. In some embodiments, the bond may be a covalent linkage. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The compounds or pharmaceutically acceptable derivatives thereof may be packaged as articles of manufacture containing packaging material and a compound or pharmaceutically acceptable derivative thereof provided herein, which is effective for modulating the activity of a skin and/or oral disorder, or for treatment, prevention or amelioration of one or more symptoms associated with a skin and/or oral disorder or in which a skin and/or oral disorder is implicated. The articles of manufacture may further comprise a label that indicates that the compound or composition, or pharmaceutically acceptable derivative thereof, is used for modulating the activity of a skin and/or oral disorder, or for treatment, prevention or amelioration of one or more symptoms associated with a skin and/or oral disorder or in which a skin and/or oral disorder is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for skin and/or oral disorders.

Embodiments of the present invention also provide kits including the elements necessary to carry out the therapies described above. Such a kit may comprise a carrier being compartmentalized to receive in close confinement therein one or more containers, such as tubes or vials. One or more of the containers may contain a compound described herein. One or more containers may contain one or more enzymes or reagents to be utilized in desired reactions. These enzymes may be present by themselves or in admixtures, in lyophilized form or in appropriate buffers. The kit may contain all of the additional elements necessary to carry out the methods of the invention.

In some embodiments, a kit of the present invention comprises a first container comprising a pharmaceutical composition of the present invention. In some embodiments, the composition comprises a pharmaceutical carrier and a compound of formula (I) or a prodrug or derivative thereof, and salts thereof.

In some embodiments, the kit may comprise a second pharmaceutical composition, wherein the second pharmaceutical composition comprises a second pharmaceutical carrier and a second therapeutic. The kit may separately store the first and second composition, optionally in separate containers. Any suitable additional therapeutic agent may be present in the second composition. In some embodiments, the second therapeutic is a therapeutic for genial warts, herpes (e.g., HSV-1), genital herpes (e.g., HSV-2), and/or herpes zoster (Shingles). In some embodiments, the second therapeutic is an agent used in antineoplastic chemotherapy or radiotherapy as described herein.

It is understood that the combinations of all embodiments described herein are also envisaged in the present invention.

The present invention will now be described in more detail with reference to the following examples. However, these examples are given for the purpose of illustration and are not to be construed as limiting the scope of the invention.

Examples

Figure 3A:
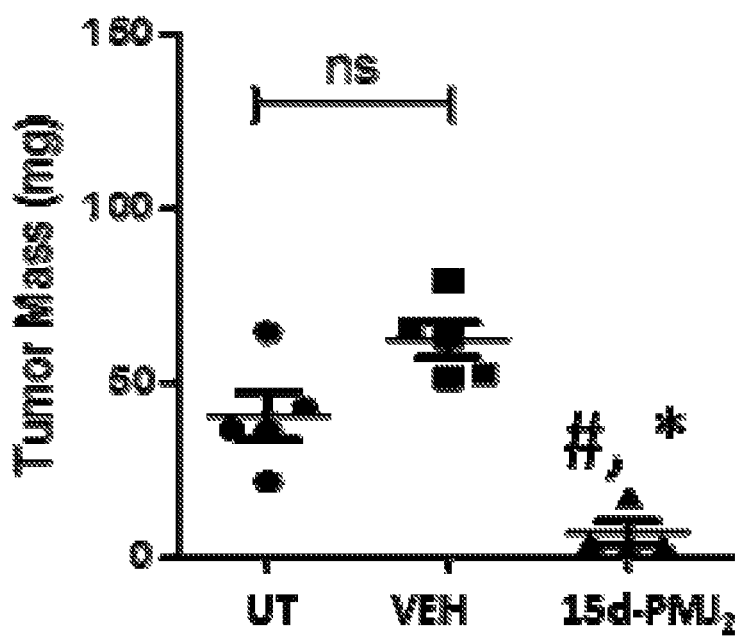
FIG. 3A is a graph illustrating that 15dPMJ2 inhibits solid tumor growth and increases ER stress. Tumors grown in C57BL/6 mice were either untreated (UT), vehicle treated (VEH), or treated with 0.5 mg/kg 15dPMJ2 for 5 days. Tumor weights were determined. #P<0.01 compared to untreated; *P<0.01 compared to vehicle treated (one-way ANOVA with Tukey's post-hoc test).
Figure 3B:
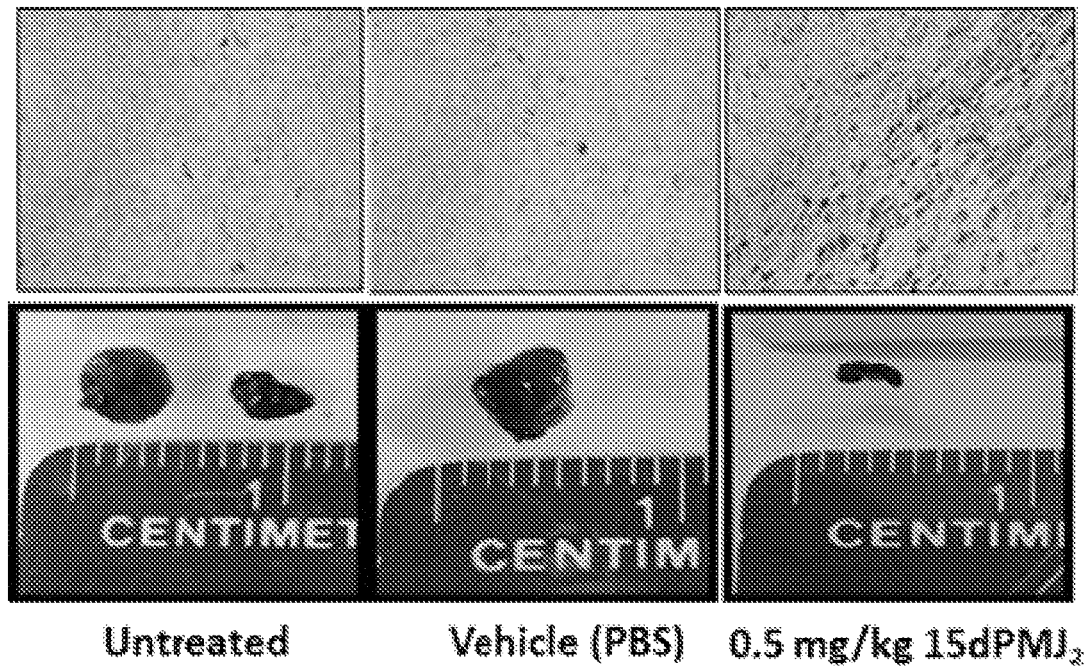
FIG. 3B shows images of CHOP-10 levels (top images) examined in the excised tumors (bottom images) as described in FIG. 3A.

Antineoplastic Activity of 15dPMJ$_2$:

To evaluate whether 15dPMJ$_2$ is selectively toxic, tumorigenic (JWF2) and non-tumorigenic (HaCaT) cells were treated with 15dPMJ$_2$ and cell viability was measured. 15dPMJ$_2$ exhibited 4-fold more toxicity towards tumorigenic keratinocytes at 5 μM which was utilized in subsequent cell culture studies (FIG. 2). To assess the in vivo antineoplastic action of 15dPMJ$_2$, the subcutaneous mouse tumor model was utilized. Melanoma cells were subcutaneously implanted in the flank region of C57BL/6 mice and treated with 0.5 mg/kg 15dPMJ$_2$, vehicle [0.1% DMSO in phosphate buffered saline (PBS)], or were untreated. 15dPMJ$_2$ caused a statistically significant reduction in tumor weight compared to vehicle and untreated animals (FIG. 3A). To determine if 15dPMJ$_2$ induced ER stress the expression of CHOP10 was detected in the tumor sections. 15dPMJ$_2$ markedly increased CHOP10 expression in the tumors (FIG. 3B). These findings suggest that 15dPMJ$_2$ will overstimulate the ER stress pathway in HPV-containing cells thereby facilitating cell death.

Since HPV also activates ER stress, topically applied prostamide 15dPMJ$_2$ may effectively eliminate cutaneous warts. Cutaneous warts are caused by HPV and include common warts, plantar warts, flat warts, and genital warts. Cutaneous warts rarely become malignant in immune competent individuals however, transformation is observed in individuals with compromised immune systems. Low-risk papillomaviruses (e.g., HPV-1, -2, -27, and -57) cause cutaneous warts whereas high-risk papillomaviruses (e.g., HPV-16 and -18) cause cervical and other epithelial carcinomas. The pathogenesis, prevention, and treatment of low- and high-risk papillomaviruses have been studied using the cottontail rabbit papillomavirus (CRPV) model in immunocompetent and immunodeficient animals, respectively.

The Effect of 15dPMJ$_7$ on Cutaneous Warts Will be Studied Using the CRPV Model.

This model has been used for several decades to examine the disease course and therapy of cutaneous warts (hereafter referred to as papillomas) because it closely recapitulates human cutaneous papillomatosis pathogenesis. 15dPMJ$_2$ will be topically applied to papillomas and normal skin to examine its effect on papilloma growth and the health of the animals, respectively.

Figure 4A:
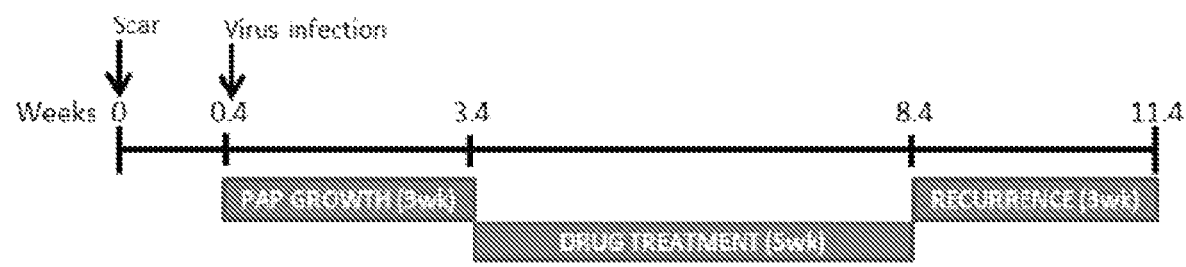
FIG. 4A is a schematic showing CRPV experimental design. Scars will be induced in animals on the dorsal surface of the rabbit. CRPV will be applied to the scar at day 3 (0.4 weeks). Papilloma growth will be monitored for 3 weeks followed by drug treatment for 5 weeks. Recurrence will be monitored for 3 additional weeks.
Figure 4B:
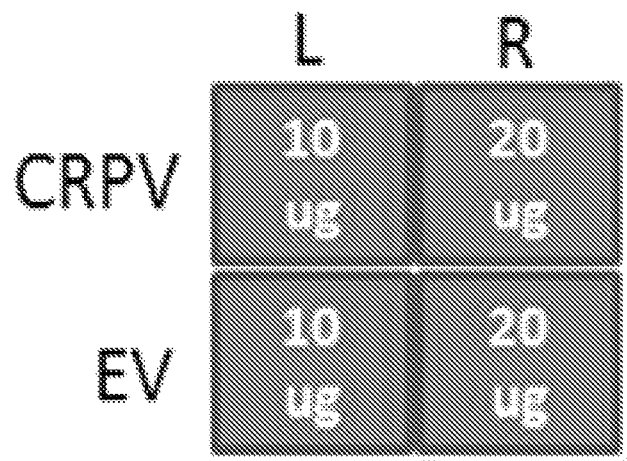
FIG. 4B is a schematic in regard to determination of viral DNA concentration. CRPV or empty vector (EV) DNA will be applied to the left (L) or right (R) scars at a concentration of 10 μg and 20 μg.
Figure 4C:
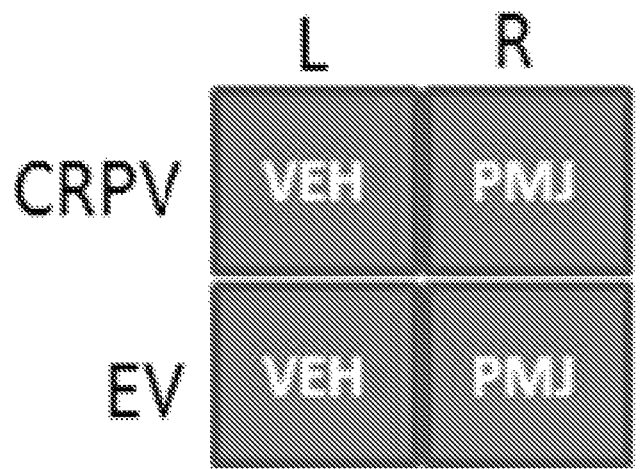
FIG. 4C is a schematic in regard to vehicle identification. 15dPMJ2 (PMJ) will be dissolved in various vehicles and topically applied to scars and normal skin. Vehicle alone will also be applied topically as a negative control.
Figure 4D:
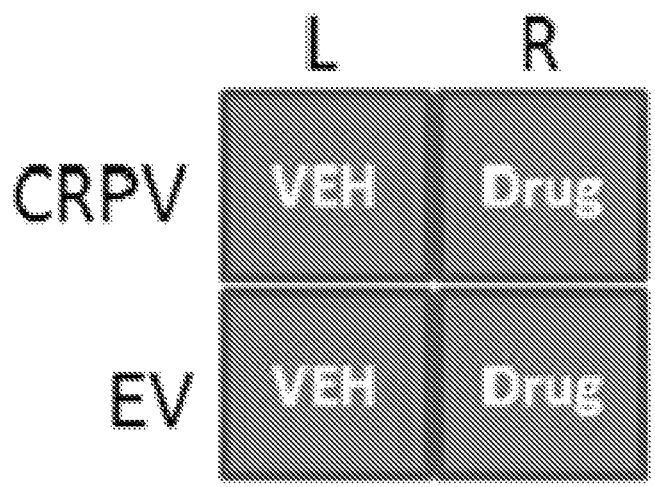
FIG. 4D is a schematic in regard to therapeutic activity. 15dPMJ2, salicylic acid or vehicle will be applied to the papillomas and the uninvolved skin.

We will utilize CRPV DNA with New Zealand White Rabbits {Christensen, N D} to determine if 15dPMJ$_2$ inhibits the growth and recurrence of papillomas. Rabbits will be anesthetized and scars formed on the skin to improve CRPV infectivity. Four scarified sites will be made on the left and right dorsal surface of the skin (total of 8 scars per animal). CRPV DNA or empty vector (EV) DNA (negative control for papilloma growth) will then be applied to the scarification sites on day 3 (FIGS. 4A-D). Virus DNA concentration determination: To determine the amount of CRPV DNA needed to form papillomas a concentration study will be conducted with 10 and 20 μg of DNA and papilloma growth monitored for 3 weeks (FIG. 4B). Drug vehicle identification: To identify the best vehicle for 15dPMJ$_2$ this agent will be dissolved in 1) phosphate buffered saline (PBS)/10% DMSO, 2) cremophor, or 3) carbomer 940 at a concentration of 0.1 mg/kg/animal. 15dPMJ$_2$ in each vehicle or the corresponding vehicle will be applied to papillomas 5 days per week for 5 weeks and papilloma growth monitored (FIG. 4C). Therapeutic effect of 15dPMJ$_2$: To determine if 15dPMJ$_2$ causes papilloma regression and/or prevents papilloma recurrence, different concentrations of 15dPMJ$_2$ in the selected vehicle (or the drug vehicle alone) will be topically applied to the papillomas (FIG. 4D). As a positive control, salicylic acid, a first-line wart treatment will also be topically administered. Drug treatment will be conducted for 5 weeks and papilloma growth monitored for three additional weeks to assess recurrence. Adverse Effects: To examine potential toxicities, 15dPMJ$_2$, salicylic acid, or vehicle will also be applied to a 2×2 cm area of uninvolved skin on papilloma-bearing animals. A dermatological examination of this skin area will be conducted 24 hours after the last drug application and at the end of the therapeutic study. Animals will then be euthanized and papillomas and the uninvolved skin collected for histological examination. To determine if topically applied 15dPMJ$_2$ causes systemic toxicity the liver, kidneys, spleen, gastrointestinal tract (GI) and blood will be collected. Tissues will be flash frozen and stored at −80 C or fixed and paraffin embedded.

Virus DNA Concentration Determination:

The concentration of CRPV DNA which produces papillomas of approximately 1 cm at week 3 will be utilized in the remaining studies. Empty vector treatment is not expected to result in papilloma formation. Drug vehicle identification: The drug vehicle which causes the greatest reduction in papilloma growth with the least amount of toxicity to the uninvolved skin will be selected to study the therapeutic effect of 15dPMJ$_2$. Therapeutic effect of 15dPMJ$_2$: Papillomas that are statistically significantly smaller in size in 15dPMJ$_2$—compared to vehicle-treated animals will establish that 15dPMJ$_2$ is an effective therapeutic agent. 15dPMJ$_2$ will be determined to inhibit recurrence if papilloma size 3 weeks after 15dPMJ$_2$ cessation is statistically significantly smaller than control group animals. Furthermore, the clinical utility of 15dPMJ$_2$ will be demonstrated if 15dPMJ$_2$ reduces papillomas size to an equal or greater extent than salicylic acid. Adverse effects: Dermal irritation of the uninvolved skin will be evaluated using a modified semi-objective, 8-point scale. 15dPMJ$_2$ will be considered non-toxic to the skin if a statistically significant difference in dermal irritation score is not observed between 15dPMJ$_2$- and vehicle-treated animals within the CRPV and EV treatment groups. Furthermore, if dermal irritation in salicylic acid treated animals is significantly greater than in 15dPMJ$_2$ treated animals, 15dPMJ$_2$ will demonstrate comparable or superior safety to a clinically utilized agent. Systemic drug toxicity will be evaluated using a five-point semi-objective scale of toxicity. 15dPMJ$_2$ will be identified as a non-toxic agent if the average body weight and morphological assessment scores of 15dPMJ$_2$-treated animals are not statistically significantly different from vehicle-treated animals within the CRPV and EV treatment groups. Alternative Approaches: If 15dPMJ$_2$ does not cause papilloma regression or recurrence, 15dPMJ$_2$ will be co-administered with clinically utilized wart treatments to assess improved activity. If 15dPMJ$_2$ exhibits significant adverse effects, alternative drug concentrations and vehicles will be tested.

That which is claimed is:

1. A method of treating melanoma comprising administering to a subject in need thereof an effective amount of a compound of formula (I) or formula (II):

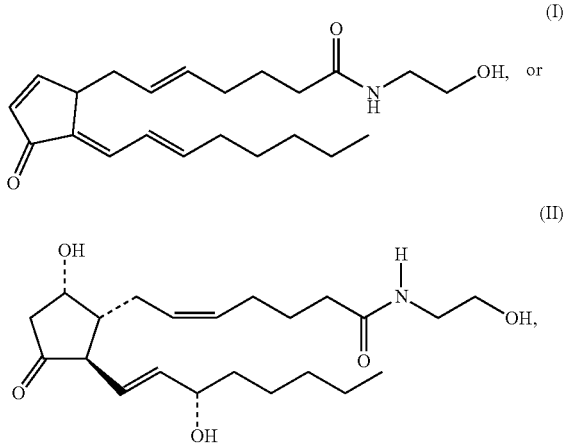

a salt thereof, or any combination thereof.

2. The method of claim 1, wherein the administration is topical administration.

3. The method of claim 1, wherein the administration is by injection and/or infusion.

4. The method of claim 1, wherein the melanoma is effected by endoplasmic reticulum (ER) stress and/or exhibits increased ER stress.

5. The method of claim 4, wherein the melanoma exhibits increased ER stress during the growth cycle of skin and/or oral cells.

6. The method of claim 1, wherein the method induces cell death in an ER-stress dependent mechanism.

7. The method of claim 1, wherein a pharmaceutical composition is administered to the subject, the pharmaceutical composition comprising the compound of formula (I) and a pharmaceutically acceptable carrier.

8. The method of claim 1, wherein the compound is the compound of formula (I) or a salt thereof.

9. The method of claim 1, wherein the compound is the compound of formula (II) or a salt thereof.

* * * * *